US010456239B2

(12) United States Patent
Yevzlin et al.

(10) Patent No.: US 10,456,239 B2
(45) Date of Patent: Oct. 29, 2019

(54) ANASTOMOTIC CONNECTOR AND SYSTEM FOR DELIVERY

(75) Inventors: Alexander S. Yevzlin, Black Earth, WI (US); Reed A. Houge, Flagstaff, AZ (US); Jeff M. Welch, Maple Grove, MN (US)

(73) Assignee: PHRAXIS INC., St. Paul, MN (US)

( * ) Notice: Subject to any disclaimer, the term of this patent is extended or adjusted under 35 U.S.C. 154(b) by 226 days.

(21) Appl. No.: 14/119,681

(22) PCT Filed: Jun. 15, 2012

(86) PCT No.: PCT/US2012/042688
§ 371 (c)(1),
(2), (4) Date: Nov. 22, 2013

(87) PCT Pub. No.: WO2012/174389
PCT Pub. Date: Dec. 20, 2012

(65) Prior Publication Data
US 2014/0088685 A1    Mar. 27, 2014

Related U.S. Application Data

(60) Provisional application No. 61/497,245, filed on Jun. 15, 2011, provisional application No. 61/497,254, (Continued)

(51) Int. Cl.
*A61F 2/07*    (2013.01)
*A61B 17/11*    (2006.01)
(Continued)

(52) U.S. Cl.
CPC ............... *A61F 2/07* (2013.01); *A61B 17/11* (2013.01); *A61F 2/064* (2013.01); *A61F 2/86* (2013.01);
(Continued)

(58) Field of Classification Search
CPC . A61B 17/11; A61B 17/1114; A61B 17/1128; A61B 17/1146; A61B 17/115;
(Continued)

(56) References Cited

U.S. PATENT DOCUMENTS 3,818,511 A    6/1974 Goldberg et al.
4,352,358 A    10/1982 Angelchik
(Continued)

FOREIGN PATENT DOCUMENTS

CA    2366703 A1    9/2000
CA    2574941 A1    7/2007
(Continued)

OTHER PUBLICATIONS

"Adjacent." Merriam-Webster.com. Accessed Dec. 26, 2016. https://www.merriam-webster.com/dictionary/adjacent.*
(Continued)

*Primary Examiner* — Elizabeth Houston
*Assistant Examiner* — Kankindi Rwego
(74) *Attorney, Agent, or Firm* — Fox Rothschild LLP

(57) ABSTRACT

An anastomotic connector comprises a vessel anchor, a midgraft connector and graft material. The vessel anchor has a generally tubular main body including a distal end and a proximal end, the distal end defining a plurality of flanges integrally formed with the tubular main body and being movable from a first loaded position to a second expanded position. The midgraft connector operably couples the graft to the vessel anchor to form an anastomotic connector between an artery and a vein.

11 Claims, 5 Drawing Sheets

Related U.S. Application Data filed on Jun. 15, 2011, provisional application No. 61/560,015, filed on Nov. 15, 2011.

(51) Int. Cl.
*A61F 2/86* (2013.01)
*A61F 2/966* (2013.01)
*A61F 2/06* (2013.01)

(52) U.S. Cl.
CPC ....... *A61F 2/966* (2013.01); *A61B 2017/1107* (2013.01); *A61B 2017/1135* (2013.01)

(58) Field of Classification Search
CPC ............ A61B 17/1152; A61B 17/1155; A61B 2017/1103; A61B 2017/1107; A61B 2017/111; A61B 2017/1117; A61B 2017/1121; A61B 2017/1125; A61B 2017/1132; A61B 2017/1135; A61B 2017/1139; A61B 2017/1142; A61B 2017/1157; A61F 2/064; A61F 2/07; A61F 2/82; A61F 2002/072; A61F 2002/075; A61F 2002/077; A61F 2002/821; A61F 2002/823; A61F 2002/825; A61F 2002/826; A61F 2002/828

See application file for complete search history.

(56) References Cited

U.S. PATENT DOCUMENTS

| | | | |
|---|---|---|---|
| 4,368,736 | A | 1/1983 | Kaster |
| 4,512,761 | A | 4/1985 | Raible |
| 5,383,892 | A | 1/1995 | Cardon |
| 5,456,712 | A | 10/1995 | Maginot |
| 5,755,775 | A | 5/1998 | Trerotola |
| 5,755,778 | A | 5/1998 | Kleshinski |
| 5,968,089 | A | 10/1999 | Krajicek |
| 5,972,017 | A | 10/1999 | Berg et al. |
| 5,989,276 | A | 11/1999 | Houser |
| 6,030,392 | A * | 2/2000 | Dakov .................. A61B 17/11 606/139 |
| 6,030,395 | A | 2/2000 | Nash et al. |
| 6,179,848 | B1 | 1/2001 | Solem |
| 6,190,590 | B1 | 2/2001 | Randall et al. |
| 6,210,429 | B1 | 4/2001 | Vardi et al. |
| 6,241,743 | B1 | 6/2001 | Levin et al. |
| 6,241,757 | B1 | 6/2001 | An |
| 6,270,524 | B1 | 8/2001 | Kim |
| 6,277,133 | B1 * | 8/2001 | Kanesaka .............. A61B 17/11 606/153 |
| 6,293,955 | B1 | 9/2001 | Houser et al. |
| 6,402,767 | B1 | 6/2002 | Nash et al. |
| 6,406,488 | B1 | 6/2002 | Tweden |
| 6,419,681 | B1 * | 7/2002 | Vargas .................. A61B 17/11 606/153 |
| 6,451,048 | B1 | 9/2002 | Berg et al. |
| 6,458,140 | B2 | 10/2002 | Akin et al. |
| 6,464,665 | B1 | 10/2002 | Heuser |
| 6,464,709 | B2 | 10/2002 | Shennib et al. |
| 6,482,214 | B1 | 11/2002 | Sidor et al. |
| 6,485,513 | B1 | 11/2002 | Fan |
| 6,517,558 | B2 | 2/2003 | Gittings et al. |
| 6,582,463 | B1 | 6/2003 | Mowry et al. |
| 6,585,760 | B1 | 7/2003 | Fogarty |
| 6,599,303 | B1 | 7/2003 | Peterson et al. |
| 6,648,901 | B2 | 11/2003 | Fleischman et al. |
| 6,682,540 | B1 | 1/2004 | Sancoff et al. |
| 6,719,781 | B1 | 4/2004 | Kim |
| 6,743,243 | B1 | 6/2004 | Roy et al. |
| 6,855,162 | B2 | 2/2005 | Parodi |
| 7,025,773 | B2 | 4/2006 | Gittings et al. |
| 7,056,326 | B2 | 6/2006 | Bolduc et al. |
| 7,105,020 | B2 | 9/2006 | Greenberg et al. |
| 7,175,652 | B2 | 2/2007 | Cook et al. |
| 7,267,680 | B2 * | 9/2007 | Wright ............... A61B 17/0644 606/151 |
| 7,591,827 | B2 | 9/2009 | Hill et al. |
| 7,611,523 | B2 | 11/2009 | Vargas et al. |
| 7,691,140 | B2 | 4/2010 | Bates et al. |
| 7,722,665 | B2 | 5/2010 | Anwar et al. |
| 7,766,955 | B2 | 8/2010 | Vardi et al. |
| 7,828,834 | B2 | 11/2010 | Garbe |
| 7,850,725 | B2 | 12/2010 | Vardi et al. |
| 7,892,247 | B2 | 2/2011 | Conston et al. |
| 7,927,343 | B2 | 4/2011 | Hill et al. |
| 8,287,586 | B2 | 10/2012 | Schaeffer et al. |
| 8,298,251 | B2 | 10/2012 | Golden et al. |
| 8,343,204 | B2 | 1/2013 | Osborne |
| 8,361,092 | B1 | 1/2013 | Asfora |
| 8,366,651 | B2 | 2/2013 | Dakin et al. |
| 8,439,963 | B2 | 5/2013 | Dickinson et al. |
| 8,486,153 | B2 | 7/2013 | Levine et al. |
| 8,551,127 | B2 | 10/2013 | Asfora et al. |
| 8,628,583 | B2 | 1/2014 | Meade et al. |
| 8,715,336 | B2 | 5/2014 | Chu et al. |
| 8,728,145 | B2 | 5/2014 | Chuter et al. |
| 2002/0022853 | A1 | 2/2002 | Swanson et al. |
| 2002/0099392 | A1 | 7/2002 | Mowry et al. |
| 2002/0099393 | A1 | 7/2002 | Fleishman |
| 2002/0123790 | A1 | 9/2002 | White et al. |
| 2003/0070676 | A1 * | 4/2003 | Cooper .................... A61B 8/12 128/200.24 |
| 2003/0109893 | A1 | 6/2003 | Vargas et al. |
| 2003/0125797 | A1 | 7/2003 | Chobotov et al. |
| 2003/0144578 | A1 | 7/2003 | Koster, Jr. |
| 2003/0176878 | A1 | 9/2003 | Bolduc |
| 2003/0216749 | A1 | 11/2003 | Ishikawa et al. |
| 2004/0093058 | A1 | 5/2004 | Cottone |
| 2004/0097991 | A1 | 5/2004 | Vargas et al. |
| 2004/0102794 | A1 | 5/2004 | Roy et al. |
| 2004/0107004 | A1 | 6/2004 | Levine et al. |
| 2004/0116946 | A1 | 6/2004 | Goldsteen et al. |
| 2004/0133221 | A1 * | 7/2004 | Sancoff ............... A61B 17/115 606/153 |
| 2005/0038455 | A1 | 2/2005 | Bates |
| 2005/0049675 | A1 | 3/2005 | Wallace |
| 2005/0049678 | A1 | 3/2005 | Cocks |
| 2005/0137677 | A1 | 6/2005 | Rush |
| 2005/0154448 | A1 | 7/2005 | Cully et al. |
| 2005/0171593 | A1 | 8/2005 | Whirley |
| 2005/0171598 | A1 | 8/2005 | Schaffer |
| 2005/0192604 | A1 | 9/2005 | Carson et al. |
| 2005/0228409 | A1 | 10/2005 | Coppi |
| 2005/0267559 | A1 | 12/2005 | De Oliveira |
| 2005/0283173 | A1 * | 12/2005 | Abbott ................. A61B 17/064 606/153 |
| 2006/0142840 | A1 | 6/2006 | Sherry et al. |
| 2007/0055358 | A1 | 3/2007 | Krolik et al. |
| 2007/0073388 | A1 | 3/2007 | Krolik et al. |
| 2007/0106313 | A1 | 5/2007 | Golden et al. |
| 2007/0179590 | A1 | 8/2007 | Lu et al. |
| 2007/0185567 | A1 | 8/2007 | Heuser et al. |
| 2007/0203572 | A1 | 8/2007 | Heuser et al. |
| 2007/0293940 | A1 * | 12/2007 | Schaeffer .................. A61F 2/07 623/1.16 |
| 2008/0082159 | A1 | 4/2008 | Tseng et al. |
| 2008/0109069 | A1 | 5/2008 | Coleman |
| 2008/0154290 | A1 | 6/2008 | Golden |
| 2008/0288044 | A1 | 11/2008 | Osbourne |
| 2009/0030502 | A1 * | 1/2009 | Sun .......................... A61F 2/07 623/1.16 |
| 2009/0036817 | A1 | 2/2009 | Dakin et al. |
| 2009/0076587 | A1 | 3/2009 | Cully et al. |
| 2009/0112237 | A1 | 4/2009 | Paul, Jr. et al. |
| 2009/0143793 | A1 | 6/2009 | Chua et al. |
| 2009/0209855 | A1 | 8/2009 | Drilling et al. |
| 2010/0010613 | A1 | 1/2010 | Dorn |
| 2010/0022940 | A1 | 1/2010 | Thompson |
| 2010/0023110 | A1 | 1/2010 | Schaeffer |
| 2010/0036401 | A1 | 2/2010 | Navia |
| 2010/0241218 | A1 | 9/2010 | Bruszewski et al. |
| 2010/0280612 | A1 | 11/2010 | Helmus |

(56) References Cited

U.S. PATENT DOCUMENTS

| | | |
|---|---|---|
| 2011/0031656 A1 | 2/2011 | Anneaux et al. |
| 2011/0118821 A1 | 5/2011 | Brocker et al. |
| 2011/0172684 A1 | 7/2011 | Granja Filho |
| 2011/0184329 A1 | 7/2011 | Kramer et al. |
| 2011/0184507 A1 | 7/2011 | Fischer, Jr. |
| 2011/0245851 A1 | 10/2011 | Ducharme |
| 2011/0264196 A1 | 10/2011 | Savage et al. |
| 2011/0282368 A1 | 11/2011 | Swayze et al. |
| 2012/0035708 A1 | 2/2012 | Paul, Jr. et al. |
| 2012/0065652 A1 | 3/2012 | Cully |
| 2012/0123513 A1 | 5/2012 | Asfora et al. |
| 2012/0290065 A1 | 11/2012 | Li et al. |
| 2013/0035752 A1 | 2/2013 | Chang |
| 2013/0085565 A1 | 4/2013 | Eller et al. |
| 2013/0274646 A1 | 10/2013 | Paris et al. |
| 2014/0031785 A1 | 1/2014 | Schwagten et al. |
| 2014/0088685 A1 | 3/2014 | Yevzlin et al. |
| 2014/0121585 A1 | 5/2014 | Baker et al. |
| 2014/0194910 A1 | 7/2014 | Orion et al. |
| 2017/0000939 A1 | 1/2017 | Cully et al. |
| 2017/0196676 A1 | 7/2017 | Donadio et al. |

FOREIGN PATENT DOCUMENTS

| | | |
|---|---|---|
| CA | 2766347 A1 | 12/2010 |
| CA | 2810671 | 3/2012 |
| JP | 2002-058594 A | 8/2002 |
| JP | 2006-510393 A | 2/2004 |
| JP | 2006-523515 A | 10/2006 |
| WO | WO 98-02099 A1 | 1/1998 |
| WO | WO-98-19629 A2 | 5/1998 |
| WO | WO-98-19636 A2 | 5/1998 |
| WO | WO 1999-45861 A1 | 9/1999 |
| WO | WO 99-62415 A1 | 12/1999 |
| WO | WO 2001-12074 A1 | 2/2001 |
| WO | WO 2001-026562 A1 | 4/2001 |
| WO | WO 2001-49213 A2 | 7/2001 |
| WO | WO 2001-49213 A3 | 7/2001 |
| WO | WO-2004-010898 A1 | 2/2004 |
| WO | WO 2002-058594 A1 | 6/2004 |
| WO | WO-2004-093966 A1 | 11/2004 |
| WO | WO2004-016201 A2 | 3/2006 |
| WO | WO 2006-028925 A1 | 3/2006 |
| WO | WO 2007-024964 A1 | 3/2007 |
| WO | WO 2008-0157283 A1 | 12/2008 |
| WO | WO-2009-055651 A1 | 4/2009 |
| WO | WO 2010-121192 A1 | 10/2010 |
| WO | WO 2012-034108 A1 | 3/2012 |
| WO | WO 2012-117402 A1 | 9/2012 |

OTHER PUBLICATIONS

Anastomosis. (n.d.). Dictionary.com Unabridged. Retrieved Jul. 30, 2017 from Dictionary.com website http://www.dictionary.com/browse/anastomosis.*

"Tine." Merriam-Webster.com. Merriam-Webster,n.d. Web. Aug. 22, 2018.*

European Search Report issued by the European Patent Office,regarding correspondence patent application Serial No. 12799745.0; dated Feb. 12, 2015; 6 pages.

European Search Report issued by the European Patent Office, regarding correspondence patent application Serial No. 12800430.6; dated Feb. 17, 2015; 6 pages.

European Search Report issued by the European Patent Office regarding correspondence patent application Serial No. 12800335.7; dated Mar. 6, 2015; 6 pages.

International Search Report and Written Opinion issued by the ISA/U.S. Receiving Office, regarding corresponding application Serial No. PCT/US2012/042639; dated Sep. 25, 2012; 9 pages.

International Search Report and Written Opinion issued by the ISA/U.S. Receiving Office, regarding corresponding application Serial No. PCT/US2012/042666; dated Sep. 13, 2012; 5 pages.

International Search Report and Written Opinion issued by the ISA/U.S. Receiving Office, regarding corresponding application Serial No. PCT/US2012/067561; dated Apr. 22, 2013; 10 pages.

Japanese Final Rejection Office Action, issued by the Japanese Patent Office regarding corresponding patent application Serial No. JP 2014-516024; dated Jun. 4, 2015; 5 pages.

Japanese Final Rejection Office Action, issued by the Japanese Patent Office regarding corresponding patent application Serial No. JP 2014-514937; dated Jun. 10, 2015; 7pages.

Japanese Rejection Office Action, issued by the Japanese Patent Office regarding corresponding patent application Serial No. JP 2014-516037; dated Jun. 4, 2015; 8 pages.

Japanese Rejection Office Action, issued by the Japanese Patent Office regarding corresponding patent application Serial No. 2015-517230; dated Nov. 16, 2015; 8 pages (English translation).

Japanese Office Action issued by the Japanese Patent Office (translated), regarding corresponding patent application Serial No. 2014-516024, dated Oct. 15, 2014; 5 pages.

Japanese Office Action issued by the Japanese Patent Office (translated), regarding corresponding patent application Serial No. 2014-514937, dated Oct. 15, 2014; 6 pages.

Japanese Office Action issued by the Japanese Patent Office (translated), regarding corresponding patent application Serial No. 2014-516037, dated Oct. 15, 2014; 5 pages.

International Search Report, U.S. Receiving Office, correspondence patent appplication: PCT/US2012/042688; dated Sep. 14, 2012, 2 pages.

European Communication pursuant to Article 94(3) EPC, issued by the European Patent Office, regarding corresponding patent application Serial No. EP 12799745.0, dated Dec. 20, 2016, 4 pages.

European Communication pursuant to Article 94(3) EPC, issued by the European Patent Office, regarding corresponding patent application Serial No. EP 12800430.6; dated Dec. 12, 2016, 4 pages.

International Search Report and Written Opinion, issued by the ISA/U.S. Receiving Office, regarding related application Serial No. PCT/US2019/017200, dated May 6, 2019; 13 pages.

International Search Report and Written Opinion, issued by the ISA/U.S. Receiving Office, regarding related application Serial No. PCT/US2019/016970, dated May 8, 2019; 13 pages.

* cited by examiner

ANASTOMOTIC CONNECTOR AND SYSTEM FOR DELIVERY

CROSS REFERENCE TO RELATED APPLICATIONS

This application is a U.S. national stage application of International application Serial No.: PCT/US2012/042688, filed on Jun. 15, 2012, which claims priority to U.S. application Ser. No. 61/497,245, filed on Jun. 15, 2011, and U.S. application Ser. No. 61/497,254, filed on Jun. 15, 2011, and U.S. application Ser. No. 61/560,015, filed on Nov. 15, 2011, the entireties of which are hereby incorporated by reference.

BACKGROUND OF THE INVENTION

Field of the Invention

This invention relates to a vascular access device for use in hemodialysis and other surgical procedures, in which short-term and long-term access is required.

Background of the Related Art

In the United States alone, approximately 400,000 people have end-stage renal disease requiring chronic hemodialysis. Hemodialysis replaces kidney function by removing toxins from the blood that are normally removed by healthy kidneys. In order to effectively remove toxins, blood must be passed at a high blood flow rate through a hemodialysis machine. This high blood flow is best achieved by the creation of a permanent vascular access site that includes an arteriovenous (AV) anastomosis in which a vein is attached to an artery to form a high-flow shunt or fistula.

Typically, a vein may be directly attached to an artery, but it can take up to twelve weeks before the fistula has sufficiently matured (time between placement and cannulation for dialysis) to provide adequate blood flow for use with hemodialysis. Moreover, a direct anastomosis may not be feasible in all patients due to anatomical considerations. Other patients may require the use of artificial graft material to provide an access site between the arterial and venous vascular systems. Because of the length of time required for a fistula to mature a patient needing dialysis will typically require a temporary access device, such as a Quinton catheter, to be inserted for hemodialysis access until the fistula has matured. The use of a temporary catheter access exposes the patient to additional risk of bleeding and infection, as well as discomfort, and is associated with a 91% higher mortality rate compared to fistulas. In trying to increase the prevalence of fistulas in the U.S., a proportional use in catheter use has been documented. What is needed is an improved vascular access device that addresses the foregoing problems.

BRIEF SUMMARY OF THE INVENTION

The present invention solves the foregoing problems by allowing a percutaneous connection to be created between an artery and vein in the arm of a kidney failure patient without the need for surgery; which allows immediate cannulation of the connection without reliance on catheter use; and which allows for the maturation of the outflow veins for subsequent conversion to a fistula.

In one aspect of the invention, an anchor device is provided. Anchor device includes a generally tubular main body having a distal end and a proximal end and defining a lumen therewithin. Generally tubular main body comprises a stented portion. The distal end, which is received within a vessel wall, includes a plurality of flanges circumferentially disposed about the distal end and integrally formed with tubular main body. The flanges may be configured to bend at an angle equal to or less than 90 degrees towards the longitudinal axis of the stented tubular main body portion or bend at an angle greater than 90 degrees away from the longitudinal axis of stented tubular main body portion. The flanges are configured to anchor the anchor device against the inner wall of a fluid passageway. Although the term "flanges" has been used herein, other anchoring structures, such as hooks, barbs, tines and other types of curved or angled fasteners, are contemplated as may be appreciated by those of ordinary skill in the art. The proximal end of stented tubular main body includes a plurality of finger-like tines integrally formed with tubular main body. Finger-like tines extend inwardly into the main body lumen. Finger-like tines are configured to securedly fasten a graft member in place within the stented tubular main body.

In another aspect of the invention, an anastomotic connector is provided that includes first and second vessel anchor devices; a graft member; and optional first and second midgraft connector members. First and second anchor devices include a generally tubular main body having a distal end and a proximal end and defining a lumen therewithin. Generally tubular main body comprises a stented portion. The distal end, which is received within a vessel wall, includes a plurality of flanges circumferentially disposed about the distal end and integrally formed with tubular main body. The flanges may be configured to bend at an angle equal to or less than 90 degrees towards the longitudinal axis of the stented tubular main body portion or bend at an angle greater than 90 degrees away from the longitudinal axis of the stented tubular main body portion. The flanges are configured to anchor the anchor device against the inner wall of a fluid passageway. The proximal end of stented tubular main body includes a plurality of finger-like tines integrally formed with tubular main body. Finger-like tines extend inwardly at an acute angle from the longitudinal axis of the tubular main body member toward the main body lumen. Graft portion comprises a generally tubular main body having a reinforced wall, the tubular body including first and second ends thereof and defining a lumen therewithin. Midgraft connector member includes first and second ends and defines a lumen therethrough. First end includes a conical-shaped head defining an aperture that provides fluid communication with the midgraft connector lumen. Second end is stepped inwardly at an approximately 90 degree angle from first end and thus includes an outer diameter that is less than the outer diameter of the first end. Second end is configured to receivably couple first end of graft portion to the midgraft connector. Graft portion fits over the second end of connector and is positioned adjacent to stepped portion. Graft portion coupled to midgraft connector member is configured to be received within stented tubular main body of anchor device. Aperture of connector member is positioned within tubular main body lumen adjacent flanges. Finger-like tines exert force against graft portion and prevent graft portion from being easily removed from anchor device. The second end of graft member is similarly connected to a midgraft connector member, which is received within the lumen of a second anchor device that is configured to be placed within a second fluid passageway. In position the first and second anchor devices fluidly couple a first fluid passageway to a second fluid passageway to form an anastomotic connector.

In another aspect of the present invention, a method of positioning a vessel anchor within a fluid passageway is provided. The method includes providing a vessel anchor, said vessel anchor including a generally tubular main body having a distal end and a proximal end, said distal end integrally defining a plurality of flanges circumferentially disposed about the distal end of said tubular main body, said tubular main body and said flanges movable between a loaded configuration and preset expanded configuration; providing a seating device comprising a wire shaft and a balloon member adapted to be inflated and deflated, said wire shaft positioned within a lumen of said tubular main body and said balloon member extending past said flanges; providing a delivery device, said delivery device including an outer sheath and an inner sheath having a lumen; compressibly loading said seating device and said vessel anchor within the lumen of said inner sheath; deploying the delivery device through an access site into a fluid passageway of a vessel; retracting the inner sheath to expose said flanges and said balloon member, wherein upon retracting the inner sheath said flanges revert to the preset expanded configuration; inflating said balloon member and causing said flanges to engage an inner surface of the fluid passageway by moving said wire shaft proximally to cause said balloon member to adjacently abut said flanges thereby seating the vessel anchor in the fluid passageway; removing said delivery device and seating device from said vessel.

In another aspect of the invention, a method of forming an anastomotic connector between two vessels in a body of a patient is provided. The method includes (i) providing a vessel anchor, said vessel anchor including a generally tubular main body having a distal end and a proximal end, said distal end integrally defining a plurality of flanges circumferentially disposed about the distal end of said tubular main body, said tubular main body and said plurality of flanges movable between a loaded configuration and preset expanded configuration; (ii) providing a seating device comprising a wire shaft and a balloon member adapted to be inflated and deflated, said wire shaft positioned within a lumen of said tubular main body and said deflated balloon member extending past said flanges; (iii) providing a delivery device, said delivery device including an outer sheath and an inner sheath defining a lumen therewithin; (iv) compressibly loading said seating device and said vessel anchor within the lumen of said inner sheath; (v) deploying the delivery device through an access site into a fluid passageway of a vessel to a predetermined position; (vi) retracting the inner sheath to expose said flanges and said balloon member, wherein upon retracting the inner sheath said flanges revert to the preset expanded configuration; (vii) inflating said balloon member and causing said flanges to engage an inner surface of the fluid passageway by proximally retracting said wire shaft to cause said balloon member to adjacently abut said flanges thereby seating the vessel anchor in the fluid passageway; (viii) retracting said outer sheath to cause said tubular main body to revert to the preset expanded configuration outside the vessel wall; (ix) operably connecting a midgraft connector to a length of graft material; (x) inserting said midgraft connector into said expanded tubular main body; (xi) withdrawing said delivery device and said seating device from said vessel; and (xii) repeating (i) through (xi) in a second vessel of a patient.

These and other features of the invention will now be described in detail with reference to the accompanying Figures.

DETAILED DESCRIPTION OF THE INVENTION

The invention is generally directed to an anastomotic connector structured to attach a dialysis graft between an artery and a vein and a novel vessel anchor for anchoring the anastomotic connector to the artery and vein. The anastomotic connectors in accordance with the invention may be placed percutaneously or subcutaneously in either an artery or a vein, and may be fabricated from any biocompatible material suitable for implantation into the human body. Further, the anastomotic connectors preferably have a low cost and are readily replaceable. As will be appreciated by those of ordinary skill in the art based upon the following disclosure, the anastomotic connectors of the invention may replace the use of catheters in those patients on hemodialysis who are permanently consigned to catheter use due to their inability (anatomically or otherwise) to sustain long-term fistula or graft options.

Numerous structural variations of an anastomotic connector device and vessel anchor are contemplated and within the intended scope of the invention. For purposes of discussion and not limitation, one exemplary embodiment will be described in detail below. As those of ordinary skill in the art will appreciate, although the anastomotic connector will be described with reference to placement within a vessel, it should be understood that the anastomotic connectors may be placed within various other fluid passageways without departing from the intended scope of the invention.

As best seen in FIGS. 1 through 6 the anastomotic connector system in accordance with the invention broadly comprises a first vessel anchor, a mid-graft connector, a graft and a second vessel anchor. The component parts of the anastomotic connector system, each comprising a separable invention, will now be described.

Figure 1:
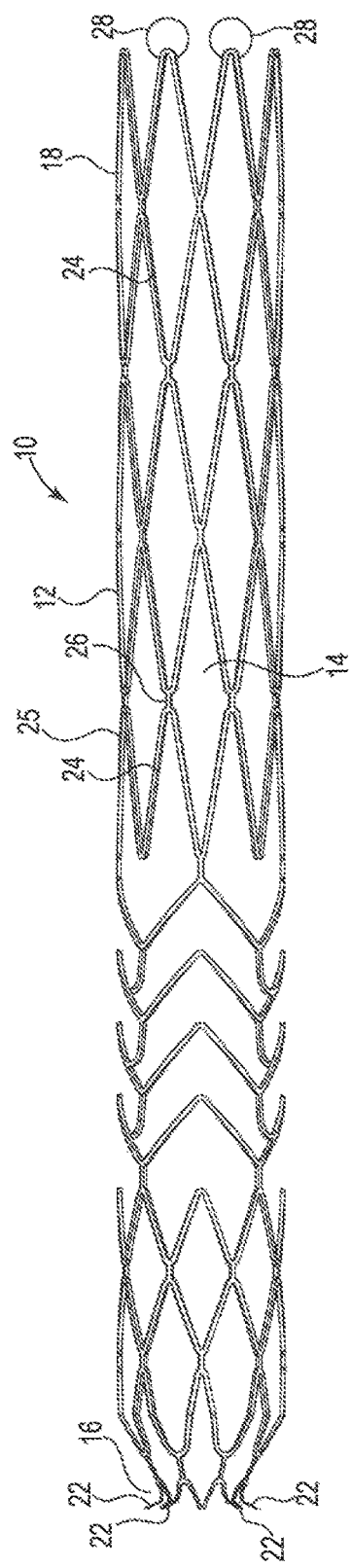
FIG. 1 is a side view of one exemplary embodiment of the vessel anchor in accordance with the invention showing a circle to indicate the general location of the tines.

FIG. 1 is a side view of one exemplary embodiment of a vessel anchor 10 used to form the anastomotic connector in accordance with the invention. As illustrated in FIG. 1, vessel 10 generally includes a tubular main body 12 defining a lumen 14 therethrough. Main body 12 includes distal 16 and proximal ends 18. In one exemplary embodiment, an internal diameter of proximal end 18 of main body 12 may be greater than an internal diameter at the distal end 16 thereof to accommodate a midgraft connector 30 and graft material 20. One exemplary but non-limiting type of graft that may be used is a Vectra® vascular access graft (Bard Peripheral Vascular, Tempe, Ariz.). However, in other embodiments the internal diameter of proximal end 18 of main body 12 may be less than the internal diameter of distal end 16, or the internal diameters may be substantially equivalent, without departing from the intended scope of the invention. The varying internal diameters of main body 12 may depend upon numerous factors such as, for example, the desired amount of flow through the anastomotic connector. In exemplary embodiments the internal diameters of the anastomotic connector may range between about 1 mm and about 10 mm, although larger or smaller internal diameters are also contemplated and within the intended scope of the invention.

Figure 5:
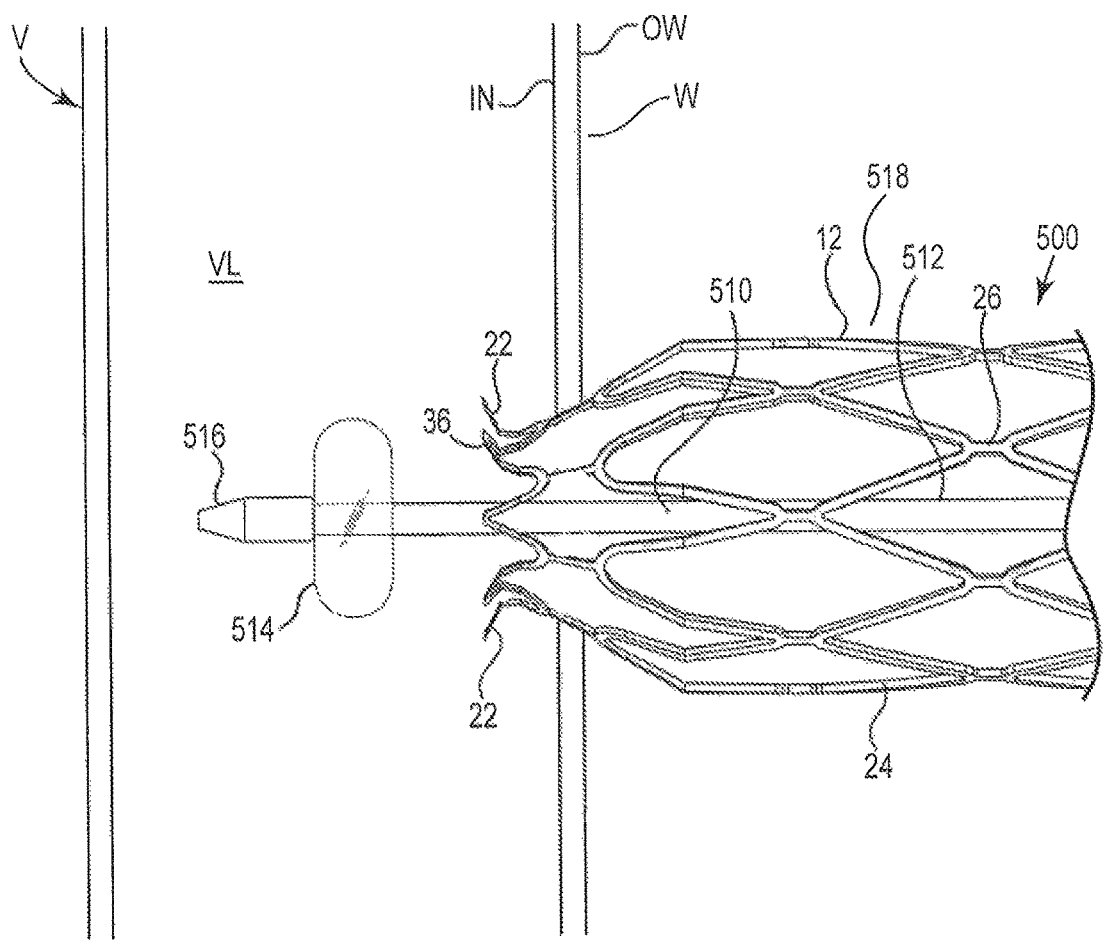
FIG. 5 illustrates the delivery device utilized to deliver the anastomotic connector in accordance with the invention.

As illustrated in FIG. 1, vessel anchor 10 includes a plurality of flanges 22 circumferentially disposed about the distal end 16 thereof. Flanges 22 are integrally formed with the tubular main body 12 of vessel anchor 10. Flanges 22 may be configured to expand upon deployment at an angle equal to or less than 90 degrees offset from the longitudinal axis of tubular main body 12 to seat the vessel anchor against a vessel wall as best seen in FIG. 5. Those of ordinary skill in the art will appreciate, however, that flanges may also be configured to expand or caused to be expanded at an angle greater than 90 degrees offset from the longitudinal axis of tubular main body 12 to seat the vessel anchor against the wall of a vessel (not shown). Those of skill in the art will also appreciate that the angle may vary depending on numerous factors, without departing from the intended scope of the invention, so long as the flanges 22 sufficiently angled to securely and firmly anchor the vessel anchor 10 to a vessel wall W.

For purposes of this disclosure, however, flanges 22 configured at an acute angle offset from the longitudinal axis of main body 12 will be discussed. Tubular main body 12 includes integrally formed struts 24 and connectors 26 fashioned in a stent-like configuration.

Vessel anchor 10 includes a plurality of finger-like tines 28 positioned at the proximal end 18 of tubular main body 12 and integrally formed therewith. Finger-like tines 28 extend inwardly into main body lumen 14 at an acute angle from the tubular main body 12. However, those of skill in the art wilt appreciate that finger-like tines 28 can extend inwardly into the main body lumen 14 at any angle that will cause them to exert a compressive force on a graft introduced therewithin. Tubular graft portion 20 is operably coupled to proximal end 18 of main body 12 by inserting it through the proximal end 18 of vessel anchor 10 toward the distal end 16 of tubular main body 12. Because finger-like tines 28 extend into the tubular main body lumen 14 they exert a compressive force on graft 20 that prevents the graft 20 from being retracted in the opposite or proximal direction thus operably coupling the tubular graft portion 20 to vessel anchor 10 assuring the graft will not dislodge after placement.

Figure 6:
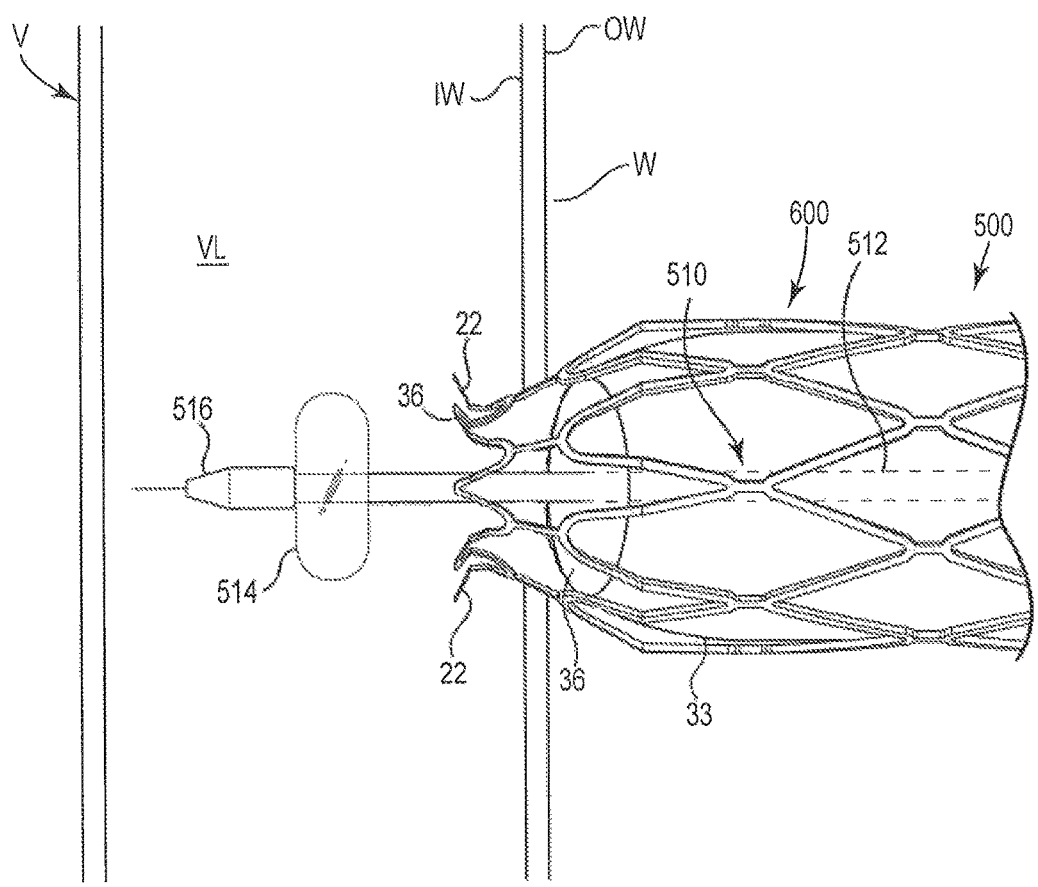
FIG. 6 is a side view illustrating the vessel anchor deployed against a vessel wall with the midgraft connector and graft received in the vessel anchor lumen in accordance with the invention.

As further illustrated in the exemplary embodiment of FIG. 1, tubular main body 12 integrally transitions at the distal and proximal ends into flanges 22 and finger-like tines 28, respectively. The central portion 25 may vary in length depending on the vessel and vessel wall into which it will be deployed. Plurality of flanges 22 are structured to move between a loaded position (inside a delivery sheath, not shown) prior to deployment and an expanded in situ position as illustrated in FIGS. 1 and 5. As will be appreciated by those of ordinary skill in the art, the anastomotic connector 600 in accordance with the invention, and as best seen in FIG. 6, is structured to provide a secure, leak-free connection to a vessel V. Vessel anchor 10 may be either self-expanding, such as so-called shape-memory materials, or non self-expanding, such as stainless steel. One benefit of using a self-expanding material is that plurality of flanges 22 will expand when deployed within a vessel without the need for a separate expansion device, thus eliminating additional equipment and steps during the deployment process.

In forming the exemplary vessel anchor 10, a tubular length of metal is used to cut the vessel anchor 10 and integrally form the struts 24 and connectors 26 of tubular main body 12 as well as flanges 22 and finger-like tines 28. As discussed previously, the metal material used in the exemplary vessel anchor 10 should be both resilient and capable of being heat treated to substantially set a desired shape. Preferably, the metal from which vessel anchor is cut exhibits a high modulus of elasticity that is biocompatible and has superior compressibility allowing the vessel anchor to be self-expandable.

One class of materials which meet these qualifications is so-called shape memory alloys. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

One particularly preferred shape memory alloy for use in the present method is Nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here.

Such NiTi alloys are preferred, at least in part, because they are commercially available, have a high yield strain and more is known about handling such alloys than other known shape memory alloys. Niti alloys are also very elastic—they are said to be "superelastic" or "pseudoelastic." This elasticity will help a device of the invention return to a present expanded configuration for deployment into a blood vessel. However, any suitable self-expanding material may be used as will be appreciated by those of ordinary skill in the art.

As hereinafter described, prior to implantation the vessel anchor 10 is collapsed inside a delivery device or sheath. Upon introduction into a vessel, the distal end of the anchoring structure freely self-expands to its original dimensions. The self-expanding behavior of the vessel anchor 10 is due to the relatively high modulus of elasticity of the shape-memory material, which imparts superior spring-like properties to the vessel anchor 10.

It is also contemplated that a woven material may be used to coat the vessel anchor 10 to ensure a leak-tight seal when implanted in the body. The woven material may be chosen to promote tissue in-growth or not. It is desirable that the material be fluid non-permeable or impermeable. Alternatively, after forming the vessel anchor as described above, a fluid impermeable, biocompatible polymer may be deposited thereon. Such a polymer will thus fill the interstices of the struts ensuring a leak-tight seal. Such biocompatible materials may include, but are not limited to, expanded Polytetrafluoroethylene ("ePTFE"), polyester, silicone composites, or various other plastics and elastomers or combinations thereof.

Figure 2:
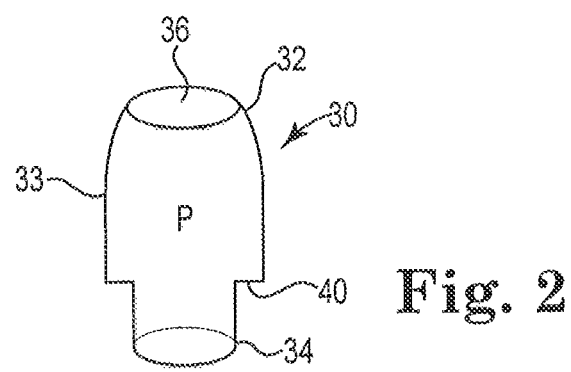
FIG. 2 is a side view of a midgraft connector utilized with the vessel anchor in accordance with the invention.
Figure 3:
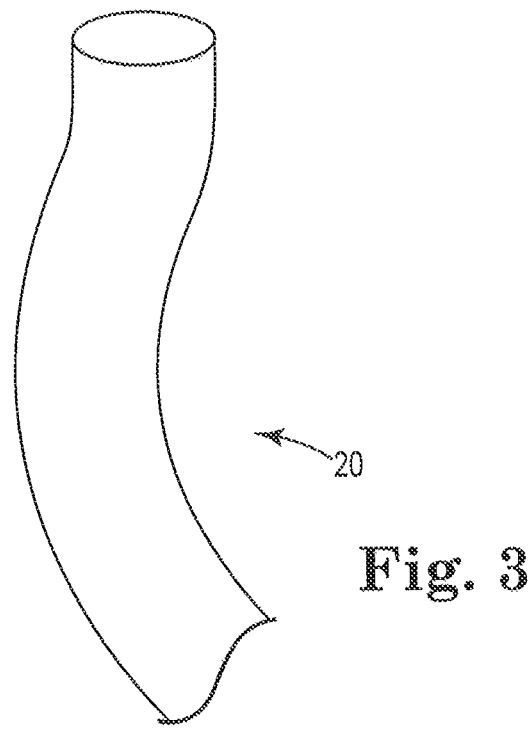
FIG. 3 illustrates a graft utilized with the system in accordance with the invention.
Figure 4:
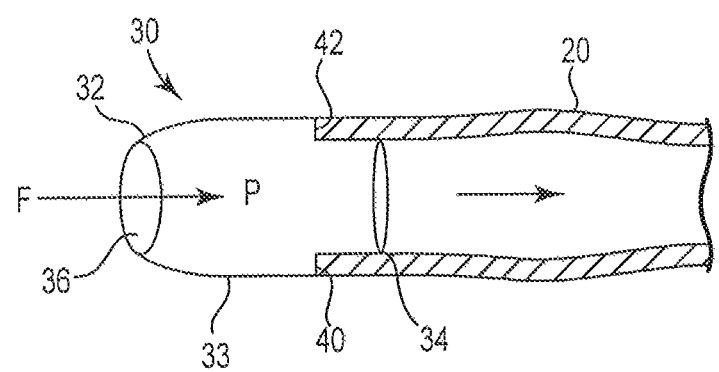
FIG. 4 depicts the graft being receivably coupled to the midgraft connector in accordance with the invention.

Referring now to FIG. 2, a perspective side view of midgraft connector 30 is depicted. Midgraft connector 30 includes first 32 and second 34 ends and main, body 33. First end 32 is substantially conical in shape and includes aperture 36. Second end 34 is open. Midgraft connector defines a passageway P for fluid flow therewithin from aperture 36 to second end 34. Second end 34 includes stepped portion 40 which is formed at an approximately 90 degree angle from midgraft connector main body 33. Thus, the outer diameter of second end 34 is sized to be smaller than the outer diameter of main body 33. Referring now to FIGS. 3 and 4, a first internal diameter of tubular graft 20 is sized substantially equivalent to or slightly smaller than the outer diameter of second end 34 of mid-graft connector 30 such that a fluid tight seal is formed between graft 24 and main body 12 when graft is operably coupled with midgraft connector 30. Midgraft connector may be fabricated from and comprise a metal such as stainless steel or other biocompatible metal or may comprise plastics or other suitable biocompatible polymers. It may also be preferable to provide the stepped portion 40 of the midgraft connector 30 with a surface that is contoured to create a smooth transition to graft material 20 to allow smooth arterial or venous blood flow into and out of the connector device. As those of ordinary skill in the art will appreciate, providing a non-thrombogenic surface minimizes the creation of recirculation or stagnation zones with high shear or dwell times that could otherwise lead to clotting.

FIG. 5 illustrates an exemplary vessel anchor 500 deployed through vessel wall W. The method of forming an anastomotic connector will now be discussed. In a technique known to those of skill in the art to gain access to a fluid passageway of a vessel, an introducer including a stylet having a micropuncture tip puncture is introduced into the patient body. The stylet is used to puncture a small access opening through vessel wall W. The stylet is then removed with the introducer remaining in position in the fluid passageway L of the vessel V through the vessel wall W.

Again referring to FIG. 5, the delivery device 510 used to deliver and seat the anchor device 500 in a vessel broadly includes a seating device 512 comprising a wire shaft portion terminating in an inflatable balloon member 514 on a distal end thereof and inner and outer sheaths (not shown). The wire shaft 512 with balloon member 514 is positioned within the lumen 14 of vessel anchor 10 with the balloon member 514 extending past aperture 36 formed by flanges 22. The combination, i.e. vessel anchor 10 and wire shaft 512 with balloon member 514 is then housed within the inner shaft (not shown) of the delivery device 510 for introduction into the fluid passageway. The delivery device 510 includes markings on the outer sheath at the proximal end which extends outside the body to enable the physician to visualize the placement of the anchor device 10 in accordance with the invention. The physician guides the delivery device into the introducer up to the first mark on the outer shaft, which extends the distal end of the delivery device into the fluid passageway of vessel V. The inner sheath is then retracted to a second marking to expose the balloon member 514 and flanges 22 in the vessel fluid passageway. The balloon member 514 is then inflated and retracted against the annular flange aperture 36 by manipulating the wire shaft 512 in a proximal direction. As the balloon member contacts the flanges 22, flanges 22 are moved to a further expanded position (due to the shape memory properties and by mechanical actuation) to secure the connector 500 to an inner surface (IN) of vessel wall W. The introducer and outer sheath are then removed. The inner sheath is retracted proximally to expose the remaining portion 518 of the vessel anchor extending outside the vessel wall W. Referring to FIG. 4, the graft material 20 is slidably coupled to the second end 34 of midgraft connector 30 until it lays adjacent stepped portion 40 to create a fluid tight seal. Introducer with micropuncture stylet is then used to puncture an access opening into graft material 20; the stylet is then removed. The free proximal end of wire shaft 512 is back loaded into the introducer to serve as a guide rail for the delivery of graft material 20 coupled to midgraft connector 30 to the portion 518 of vessel anchor extending outside the vessel wall. The introducer is removed from the graft material and with balloon member inflated the graft material is delivered over the wire shaft 512 into the lumen of the vessel anchor until the conical head of midgraft connector lay outside the vessel wall adjacent aperture 36. Midgraft connector provides strength and stability to vessel anchor to reduce the likelihood that it will collapse during use. Balloon member 514 is then deflated and wire shaft 512 is removed from the system leaving the vessel anchor seated in the vessel fluid passageway and operably coupled to graft material 20 via midgraft connector 30. The foregoing process is then repeated in a second vessel to form the anastomotic connector in accordance with the invention.

Additionally, it may be preferable to provide the anastomotic connectors of the invention with an inner surface that is contoured to allow smooth arterial or venous blood flow into and out of the connector device. As those of ordinary skill in the art will appreciate, providing a non-thrombogenic surface minimizes the creation of recirculation or stagnation zones with high shear or dwell times that could otherwise lead to clotting.

It is also contemplated that the inner or outer surface of the anastomotic connectors of the invention be configured to deliver and release therapeutic substances such as anti-microbial agents, anti-inflammatory agents, anti-proliferative agents (e.g. taclipaxel), growth factors, stem cells, collagen and the like. Those of ordinary skill in the art will appreciate that these therapeutic agents may be coupled with the connector and/or the external or internal surface of the connector by means such as being encased or embedded in a polymeric or other biocompatible coating, applied to a textured external surface of the connector; contained within pockets of the connector on either an internal or external surface, and the like.

As will be appreciated by those of ordinary skill in the art, the same general process described herein may be followed in order to place a connector within other types of fluid passageways. Although a method of deploying an anastomotic connector having a self-expanding anchor member has been generally described herein, the method may be adapted for deploying an anastomotic connector having a non self-expanding anchor member.

Based upon the present disclosure and after viewing the exemplary embodiment of the anastomotic connector presented herein, the many advantages and benefits provided by the invention will be appreciated by those of ordinary skill in the art. One advantage is that the geometry of the anastomotic connector allows continuous and uninterrupted arterial or venous flow during use for dialysis or other applications, thereby eliminating or substantially reducing any loss of circulation to the downstream, distal extremities. Stated alternatively, the geometry of the anastomotic connectors allows "full" flow into the graft as well as "full" flow to the downstream anatomy. Thus, distal arterial flow is not "cutoff" due to the presence of the anastomotic connector. Another advantage is that the anastomotic connectors of the invention may be implanted percutaneously rather than with an "open surgery" approach. The implantation method is therefore less invasive for the patient and faster for the surgeon. Yet another advantage is that the present invention allows for maturation of the distal vein in preparation for secondary AVF while avoiding a central dialysis catheter.

Although the present invention has been described with reference to preferred embodiments, those of ordinary skill in the art will recognize that changes may be made in form and detail without departing from the spirit and scope of the invention.

What is claimed is:

1. A vessel anchor for use in an arteriovenous anastomotic connector device comprising:
   an arteriovenous anastomotic connector device having an elastic tubular main body defining a lumen therewithin and formed from a plurality of struts and connectors, said elastic tubular main body including a distal end and a proximal end;
   a plurality of flanges each having first and second flange ends integrally formed with said tubular main body and a third flange tip end, said plurality of flanges movable between a loaded position and an expanded position, wherein in the expanded position the flanges seat said vessel anchor against an inner wall of an artery, and
   a plurality of finger-like tines, each having a first tine end integrally formed with said tubular main body adjacent said proximal end and an unattached, second tine end that extends inwardly into the lumen of said main body at an acute angle, wherein said arteriovenous anastomotic connector device connects a fluid blood flow in an artery to a fluid blood flow in a vein.

2. The vessel anchor of claim 1 wherein said plurality of flanges are offset from a longitudinal axis of said tubular main body by an acute angle.

3. The vessel anchor of claim 1 wherein said plurality of flanges are offset from a longitudinal axis of said tubular main body by an angle equal to or greater than 90 degrees.

4. The vessel anchor of claim 1 wherein an inner diameter at said proximal end of the main tubular body is larger than an inner diameter at said distal end.

5. The vessel anchor of claim 1 wherein said plurality of finger-like tines exert a compressive force on a graft.

6. The vessel anchor of claim 1 wherein said vessel anchor is formed from a shape memory material.

7. The vessel anchor of claim 1 wherein said plurality of flanges are circumferentially disposed about the distal end.

8. The vessel anchor of claim 7 wherein said tubular main body comprises a plurality of struts and connectors forming a stent.

9. The vessel anchor of claim 1 wherein said vessel anchor is coated with a fluid impermeable material.

10. The vessel anchor of claim 9 wherein said fluid impermeable material is woven.

11. The vessel anchor of claim 9 wherein said fluid impermeable material is a polymeric material.

* * * * *